United States Patent
Ravnås (10) Patent No.: US 10,876,375 B2
(45) Date of Patent: *Dec. 29, 2020

(54) RESERVOIR TREATMENTS

(71) Applicant: GOE-IP AS, Hafrsfjord (NO)

(72) Inventor: Asle Ravnås, Hafrsfjord (NO)

(73) Assignee: GOE-IP AS, Hafrsfjord (NO)

(*) Notice: Subject to any disclaimer, the term of this patent is extended or adjusted under 35 U.S.C. 154(b) by 0 days.

This patent is subject to a terminal disclaimer.

(21) Appl. No.: 16/510,598

(22) Filed: Jul. 12, 2019

(65) Prior Publication Data

US 2019/0360298 A1    Nov. 28, 2019

Related U.S. Application Data (63) Continuation of application No. 15/738,381, filed as application No. PCT/EP2016/064895 on Jun. 27, 2016, now Pat. No. 10,385,652.

(30) Foreign Application Priority Data

Jun. 25, 2015 (GB) .................................. 1511218.8

(51) Int. Cl.
*E21B 33/13* (2006.01)
*C09K 8/516* (2006.01)
(Continued)

(52) U.S. Cl.
CPC .............. *E21B 33/13* (2013.01); *C09K 8/426* (2013.01); *C09K 8/516* (2013.01); *C09K 8/582* (2013.01); *C09K 8/92* (2013.01); *C09K 2208/24* (2013.01)

(58) Field of Classification Search
None
See application file for complete search history.

(56) References Cited

U.S. PATENT DOCUMENTS 3,724,548 A * 4/1973 Parker .................... E21B 43/20
166/275
3,749,171 A * 7/1973 Marx .................... E21B 33/138
166/270

(Continued)

FOREIGN PATENT DOCUMENTS

CA        2610894 A1    6/2008
CA        2903710 A1    9/2014
(Continued)

OTHER PUBLICATIONS

Kaihe, Lv, "The technique of protecting hydrocarbon reservoir," 2 pages, (translation not available at this time).
(Continued)

*Primary Examiner* — Anuradha Ahuja
(74) *Attorney, Agent, or Firm* — Meunier Carlin & Curfman LLC (57) ABSTRACT

Provided herein is a method of establishing a plug in a hydrocarbon reservoir, the method comprising introducing into the reservoir a formulation comprising solid particles and a viscosifier and then reducing the viscosity of said viscosifier, thereby causing said solid particles to form a plug within said hydrocarbon reservoir. Also provided is a method of establishing a plug in a hydrocarbon reservoir, the method comprising introducing into the reservoir a formulation comprising:
(a) microorganisms or cell-free enzymes;
(b) solid particles; and
(c) a viscosifier which is a substrate for the microorganisms or cell-free enzymes of (a).
Also provided is a formulation comprising:
(a) microorganisms or cell-free enzymes;
(b) solid particles made from wood or a wood derived product; and
(c) a viscosifier which is a substrate for the microorganisms or cell-free enzymes of (a).

18 Claims, 7 Drawing Sheets

(51) Int. Cl.
*C09K 8/582* (2006.01)
*C09K 8/42* (2006.01)
*C09K 8/92* (2006.01)

(56) References Cited

U.S. PATENT DOCUMENTS

| | | | |
|---|---|---|---|
| 3,766,984 A | 10/1973 | Nimerick | |
| 4,157,116 A * | 6/1979 | Coulter | E21B 33/138 166/280.1 |
| 4,485,020 A | 11/1984 | Shay et al. | |
| 4,716,966 A | 1/1988 | Shu | |
| 4,906,575 A * | 3/1990 | Silver | C09K 8/905 435/243 |
| 4,941,533 A * | 7/1990 | Buller | C09K 8/594 166/246 |
| 4,947,932 A | 8/1990 | Silver et al. | |
| 5,010,954 A | 4/1991 | Falk | |
| 5,028,344 A | 7/1991 | Hoskin | |
| 5,083,611 A * | 1/1992 | Clark | C09K 8/905 166/246 |
| 5,304,620 A | 4/1994 | Holtmyer et al. | |
| 5,339,900 A * | 8/1994 | Clough | C09K 8/54 166/279 |
| 5,350,528 A | 9/1994 | Westland et al. | |
| 5,362,713 A * | 11/1994 | Westland | C09K 8/206 507/110 |
| 6,059,034 A * | 5/2000 | Rickards | C09K 8/80 166/280.2 |
| 6,734,298 B1 | 5/2004 | Barbucci et al. | |
| 8,936,086 B2 | 1/2015 | Liang et al. | |
| 2002/0169083 A1* | 11/2002 | Krosigk | C09K 8/02 507/100 |
| 2006/0019834 A1* | 1/2006 | Melbouci | C09K 8/04 507/100 |
| 2007/0178569 A1* | 8/2007 | Leschine | C12N 1/26 435/161 |
| 2010/0036017 A1* | 2/2010 | Eoff | C04B 28/02 523/130 |
| 2012/0073809 A1 | 3/2012 | Clum et al. | |
| 2012/0273189 A1 | 11/2012 | Alsop et al. | |
| 2012/0285692 A1 | 11/2012 | Potapenko et al. | |
| 2013/0081813 A1* | 4/2013 | Liang | C09K 8/035 166/282 |
| 2014/0017735 A1* | 1/2014 | Brunecky | C12P 7/14 435/99 |
| 2014/0083679 A1* | 3/2014 | Ravnas | E21B 33/138 166/243 |
| 2014/0158354 A1* | 6/2014 | Kumar | E21B 21/003 166/293 |
| 2014/0315765 A1 | 10/2014 | McDaniel | |
| 2014/0353042 A1* | 12/2014 | Karale | C09K 8/04 175/64 |
| 2015/0265999 A1* | 9/2015 | Medoff | C08L 97/02 204/157.63 |
| 2016/0002521 A1* | 1/2016 | Dillon | C09K 8/06 507/101 |
| 2016/0076014 A1* | 3/2016 | Medoff | C12P 7/56 435/100 |
| 2016/0108695 A1* | 4/2016 | Okura | E21B 33/12 166/376 |

FOREIGN PATENT DOCUMENTS

| | | |
|---|---|---|
| CN | 1940008 A | 4/2007 |
| CN | 102559162 A | 7/2012 |
| CN | 103189599 A | 7/2013 |
| CN | 103562340 | 2/2014 |
| CN | 104531115 | 4/2015 |
| GB | 2246586 | 5/1992 |
| WO | 2012042403 | 4/2012 |
| WO | 2012164285 | 12/2012 |

OTHER PUBLICATIONS

International Search Report dated Sep. 19, 2016, from International Application No. PCT/EP2016/064895, 12 pages.
Sissons et al. Applied and Environmental Microbiology, Apr. 1987, p. 832-838.
Ugelstad et al. Adv. Colloid Interface Sci. 13, 101 (1980).
Ugelstad et al. J. Polym. Sci 72, 225 (1985).
Ugelstad et al. Makromol. Chem. Suppl. 10/11, 215 (1985).
Freier et al. (1988) Applied and Environmental Biology, vol. 54, No. 1, p. 204-211.
Liu et al., Process Biochemistry 40 (2005) 3701-3706.
Muchová et al., Water Science and Technology (2009), vol. 60, issue 4, p. 965-973.
Nankai et al., Applied and Environmental Microbiology, Jun. 1999, p. 2520-2526.
Cadmus et al., Applied and Environmental Microbiology, Jul. 1982, p. 5-11.
Sutherland, Journal of General Microbiology, 1987, 133, p. 3129-3134.
Cord-Ruwisch et al. (1987) Sulfate-reducing bacteria and their activities in oil production, Journal of Petroleum Technology, vol. 39, issue 1.
Reynolds PHS et al. Applied and Environmental Microbiology, Jan. 1986, p. 12-17.
Schmidt et al. Applied Rheology vol. 23 Issue 5 (2013).
Ehrenberg and Nadeau, The American Association of Petroleum Geologists, vol. 89, No. 4, Apr. 2005, p. 435-445.
Fei et al. Journal of Applied Polymer Science, vol. 78, issue 2, p. 278-283, Oct. 2000 (Abstract Only).
Qian et al. Journal of Applied Microbiology, vol. 102, p. 1362-1371, 2007.
Product Data Sheet CELPOL® R Polyanionic Cellulose, Kelco Oil Field Group, May 31, 2011.
Product Data Sheet CELPOL® RX Polyanionic Cellulose, Kelco Oil Field Group, May 31, 2011.
Product Data Sheet CELPOL® SLX Polyanionic Cellulose, Kelco Oil Field Group, May 31, 2011.
Product Data Sheet XANVIS®, Kelco Oil Field Group, Jul. 31, 2009.
Product Data Sheet GEOVIS® XT, Kelco Oil Field Group, May 29, 2012.
Search and Examination Report, issued by the UKIPO in Application No. GB 1511218.8, dated Mar. 11, 2016.

* cited by examiner

RESERVOIR TREATMENTS

This application is a continuation of U.S. application Ser. No. 15/738,381, filed on Dec. 20, 2017, which is a a national stage application filed under 35 U.S.C. § 371 of PCT/EP2016/064895, filed Jun. 27, 2016, which claims priority to European Patent Application Serial No. 1511218.8, filed on Jun. 25, 2015, the disclosures of which are expressly incorporated herein by reference in their entirety.

The present invention relates to a method of treating a hydrocarbon reservoir in order to prepare it for extraction of hydrocarbons therefrom and to formulations for use in such methods. More particularly, the methods relate to plugging of a hydrocarbon reservoir in order to alter the flow of liquid through the reservoir.

Many hydrocarbon reservoirs have a primary production phase where a production well drilled into the formation results in travel of oil to the surface; the reservoir drives come from natural mechanisms, optionally enhanced by pumps. Later in the working life of a reservoir pressure will fall and a liquid, often water, may be pumped via an injection well into the formation to force the hydrocarbon, usually oil, through the formation and into the production well. This is the secondary recovery phase. Over time, certain reservoirs, in particular carbonate reservoirs, will experience a steep decline in production as oil found within the matrix of the formation is not readily flushed out. The injection liquid will follow a path where the flow resistance is at its least, a flow channel, also referred to as a connected fracture system or water thief zone. In the case of a carbonate reservoir this will typically be a fracture within the matrix formed as a result of chalk erosion. Erosion may be chemical or physical. Erosion is increased by the pressure from liquid injection and increased flow rate through the matrix. As a consequence water penetration of the matrix is limited.

Carbonate rocks (chalk and limestone) account for more than half of the world's hydrocarbon reservoirs. Carbonate reservoirs typically comprise a matrix, which provides the main oil storage capacity, and have fractures within the matrix. There is a need for improved methods of recovering oil from carbonate reservoirs.

It is possible to calculate or model how the injection liquid flows in the reservoir. For example, it is known for low-level radioisotopes with relatively short half-lives to be added as tracers to the injection water. Radiation from the isotopes can be identified in the production well. It is thus possible to estimate the time it takes for the injection liquid to pass from the injection well to the production well. Alternatively, specific chemicals, for example nitrate, can be used as trace substance.

Figure 1:
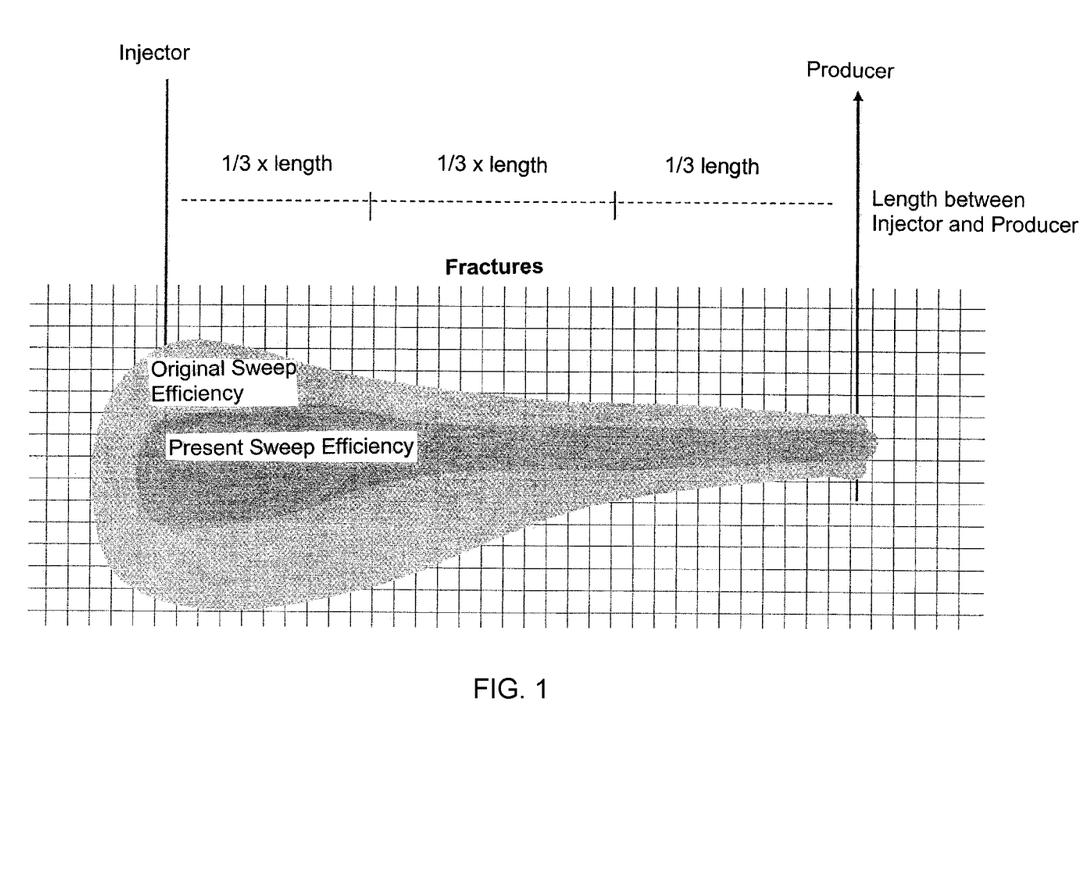
FIG. 1—is a drawing showing how the formation of dominant fractures between Injector and Producer holes result in reduced Sweep Efficiency through a matrix.

The ability of the injection liquid to force the oil forwards is referred to in the field as the sweep efficiency of the injection liquid. Water thief zones caused by dominant fractures between injection and producer holes acting as flow channels will reduce the sweep efficiency (FIG. 1). It is known that the sweep efficiency of the injection liquid can be improved if a plug is formed in the fracture system. The plug can be partially permeable, but the flow resistance increases such that the injection liquid is forced to flow around the plug and thus into those parts of the reservoir that now have the least flow resistance. The sweep efficiency of the injection liquid is improved in this way. Ideally the sweep efficiency as compared to the original sweep efficiency will be enhanced but a return to the original sweep efficiency will still result in improved oil recovery. Plugs in the middle third (FIG. 1) may improve the sweep efficiency beyond that of the original sweep efficiency.

Plugs can be produced by admixing gel-forming, water-soluble polymers to the injection water. The polymers can be synthetic, for example polyacrylamide, or biological. Xanthan, for example, is used as a biopolymer and is discussed inter alia in patent documents U.S. Pat. Nos. 4,716,966, 4,485,020, 4,947,932, and GB 2,246,586. Patent document U.S. Pat. No. 5,028,344 discusses the use of cellulose and modified cellulose, while patent document U.S. Pat. No. 5,010,954 discusses the use of guar gum and carboxymethylcellulose.

It is disclosed in WO 2012/164285 how a plug may be generated which relies on microbial biomass, such a 'living plug' offers benefits in terms of plug control. However, it requires a continuous supply of nutrients which may be costly; in some circumstances, a static plug which does not require a continuous supply of nutrients would be desirable.

When attempting to plug a reservoir it is especially difficult to ensure that the right zone is plugged; in particular there is a need to provide a plug which can travel through the reservoir to a target position. It would be undesirable if the plug introduced into the reservoir had such a high tendency to plug that it blocked fractures adjacent to the injection point. On the other hand, a plug must be able to withstand significant pressures if it is to stand firm and force water into the surrounding matrix. Prior to the present invention, no plugging systems have been described which enable plugging remotely from the injection well, i.e. deep into the reservoir.

The present inventor has developed a plugging system that addresses these needs and in one aspect the present invention provides a formulation comprising:
(a) microorganisms (including those which are mesophiles, thermophiles, extreme thermophiles or hyperthermophiles);
(b) solid particles, preferably made from wood or other cellulosic material;
(c) a viscosifier which is a substrate for the microorganisms of (a); and optionally
(d) growth medium.

In preferred embodiments is provided a formulation comprising:
(a) microorganisms which are:
   (i) mesophiles, thermophiles, extreme thermophiles or hyperthermophiles,
   (ii) unable to utilise hydrocarbons as a carbon source,
   (iii) not indigenous to the hydrocarbon reservoir, and optionally
   (iv) cellulolytic or hemicellulolytic;
(b) solid particles, preferably made from wood or other cellulosic material;
(c) a viscosifier which is a substrate for the microorganisms of (a); and optionally
(d) growth medium.

Thermophiles, extreme thermophiles or hyperthermophiles are generally preferred.

The formulation is introduced into the reservoir in the form of a liquid suspension which is mobile within the flow channels of the reservoir. As a result of the interactions of the components within the formulation, the suspension converts into a mass which can effectively plug one or more fractures or channels within the reservoir. This transition from mobile liquid to pluggable mass is achieved because the microorganisms degrade the viscosifier which had served to reduce the overall friction of the formulation, allowing it to pass as a cohesive and mobile slug through the reservoir. The viscosifier had enabled the suspension to flow through the reservoir, when this is removed the particles can be packed by back pressure and press against the walls of the flow channel, expelling liquid from within the formulation and causing a plug mass. Total friction of the particles against each other and against the walls withstands the back pressure; the longer the plug the greater the friction and the greater the forces which can be withstood.

The formulation of the invention is intended for introduction into a hydrocarbon reservoir and is provided in suitable containers, e.g. a container with a capacity of at least 25 litres, preferably at least 100 litres, more preferably at least 500 or 1000 litres. Thus the formulation will typically be provided in these volumes, or ready to be generated in these volumes on addition of water to the desired viscosity.

Each injection of the formulation of the invention into the reservoir will be of around 10-100 m$^3$, preferably 30-70 m$^3$.

The microorganisms may be capable of sporulation and it may be preferred to include them as spores in the formulation which is introduced into the reservoir.

The microorganisms are preferably unable to utilise hydrocarbons (i.e. downhole oil and gas reserves) as a carbon source, i.e. preferably cannot support their own growth exclusively in hydrocarbons as a source of carbon. However, as shown in the Examples, while the microorganisms will typically not grow within the oil, the presence of oil may not be toxic. In general, the microorganisms do not thrive outside the environment of the slug.

For performance of the invention there is an essential relationship between the microorganisms and viscosifier, namely that the microorganisms can degrade the viscosifier and, preferably, the viscosifier can act as sole or primary carbon source for the microorganisms. As discussed in more detail below, the viscosifier also serves to reduce friction and acts as a carrier, allowing the whole formulation to move through flow channels in the reservoir.

The microorganisms are able to degrade the viscosifier and are preferably saccharolytic (e.g. polysaccharolytic) or lignocellulolytic, more preferably cellulolytic or hemicellulolytic.

Thus, the viscosifier is preferably a polysaccharide or derivative thereof or derived from lignin. The viscosifier will typically be a polymer in order that it has the physical properties to perform its carrier function. A low molecular weight viscosifier such as glycerol may be used together with a high molecular weight degradable polymer. The primary polymeric viscosifiers typically have a weight average molecular weight of 50,000-500,000.

The viscosifier will typically have a high molecular weight so that it can provide high viscosity and low friction (acting as a lubricant) until it is degraded. In addition to a high molecular weight component, a further viscosifying substrate may be used, e.g. glycerol.

Cellulolytic and hemicellulolytic microorganisms are able to grow on cellulose and/or hemicellulose. Most cellulolytic organisms are also hemicellulolytic. Preferably the microorganisms are able to utilise cellulose and/or hemicellulose as sole carbon source. In practice they can also use other carbon sources, in particular derivatives and degradation products of these complex polysaccharides, such as carboxymethyl cellulose (CMC). 'Hemicellulose' encompasses a wide variety of hetero-polysaccharides, the polysaccharides are typically branched and amorphous and may comprise many different sugar monomers, e.g. xylose, mannose, galactose, arabinose. Cellulose, in contrast, consists only of glucose monomers.

The microorganisms are preferably bacteria. Preferred bacteria according to the invention include the cellulolytic bacteria *Clostridium thermocellum* and *Acidothermus cellulolyticus*. Different reservoirs are at different temperatures and the microorganisms can be selected accordingly; *A. cellulolyticus* thrives at higher temperatures than *C. thermocellum* and so is more suitable for hotter reservoirs. *C. thermocellum* is especially preferred and the strain known as JW20 (ATCC 31549) is most preferred. Further suitable bacteria are described by Sissons et al. in Applied and Environmental Microbiology, April 1987, p 832-838, in particular the strain designated TP8.T and deposited under the name *Caldicellulosiruptor saccharolyticus* (ATCC 43494).

Further suitable cellulolytic bacteria include: *Caldocellulosiruptor saccharolyticus, Caldocellulosiruptor lactoaceticus, Caldocellulosiruptor kristjanssonii, Anaerocellum thermophilium, Butyrivibrio fibrisolvens, Ruminococcus flavefaciens, Ruminococcus succinogenes, Ruminococcus albus, Eubacterium cellulolyticum, Clostridium acetobutylicum, Clostridium chartatabidum, Clostridium cellulovorans, Clostridium herbivorans, Clostridium cellulosi, Clostridium cellobioparum, Clostridium papyrosolvens, Clostridium josui, Clostridium cellulolyticum, Clostridium aldrichii, Clostridium stercorarium, Clostridium thermocellum, Clostridium cellulofermentans, Clostridium celerescens, Clostridium thermopapyrolyticum, Clostridium thermocopriae, Clostridium* sp. C7, *Bacteroides* sp. P-1, *Bacteroides cellulosolvens, Acetivibrio cellulolyticus, Acetivibrio cellulosolvens, Thermoactinomyces* sp. YX, *Caldibacillus cellulovorans, Bacillus circulans, Acidothermus cellulolyticus, Cellulomonas biazotea, Cellulomonas cartae, Cellulomonas cellasea, Cellulomonas cellulans, Cellulomonas fimi, Cellulomonas flavigena, Cellulomonas gelida, Cellulomonas iranensis, Cellulomonas persica, Cellulomonas uda, Curtobacterium falcumfaciens, Micromonospora melonosporea, Actinoplanes aurantiaca, Streptomyces reticuli, Streptomyces alboguseolus, Streptomyces aureofaciens, Streptomyces cellulolyticus, Streptomyces flavogriseus, Streptomyces lividans, Streptomyces nitrosporeus, Streptomyces olivochromogenes, Streptomyces rochei, Streptomyces thermovulgaris, Streptomyces viridosporus, Thermobifida alba, Thermobifida fusca (Thermomonospora), Thermobifida cellulolytica, Thermomonospora curvata, Microbispora bispora, Fibrobacter succinogenes, Sporocytophaga myxococcoides, Cytophaga* sp., *Flavobacterium johnsoniae, Achromobacter piechaudii, Xanthomonas* sp., *Cellvibrio vulgaris/fulvus, Cellvibrio gilvus, Cellvibrio mixtus, Pseudomonas fluorescens (cellulosa), Pseudomonas mendocina, Myxobacter* sp. AL-1.

The microorganisms can conveniently be grown in fermenters. It may be desired to transport and/or inject the bacteria in spore form. Keeping the microorganisms cool and/or manipulating pH can maintain them in spore form.

The particles are preferably made from solid wood, e.g. *Corylus*, preferably *Corylus avellana* (hazel), *Pinus* (pine), *Betula* (birch) and *Quercus* (oak). Wood is the lignocellulosic material found between the pith and bark of a tree or shrub. Alternatively the particles may be made from a wood derived product, e.g. hardboard, particle board, MDF etc. Such products typically comprise wood fragments and a polymeric binder such as a resin, the products generally being produced at high temperatures and under pressure.

The particles are able, when packed together, to form a plug in a fracture which is sufficiently resistant to pressure generated by injection liquid that the plug can force injection liquid into the matrix around the fracture or channel. Thus solid particles according to the present invention when present in water or in another low viscosity environment can form a plug which interrupts liquid flow through a hydrocarbon reservoir.

The particles may be made from non-cellulose based polymeric materials, both naturally occurring and synthetic or chemical crystals. The functional requirements of the particles are described herein and suitable materials can be selected to deliver these properties. Deformable polymeric particles may be made, for example, from polyacrylamide. Such particles may be nanoparticles.

A further type of suitable solid particles are so called Ugelstad particles, produced by their Method #2, or more preferably by their Method #3, the 'Ugelstad Process', a two-step swelling process based on polymer seed particles. The seed particles are activated (swollen) by a solvent which is then removed allowing high levels of monomer uptake. This process is very flexible and allows the size, density and deformability of the particles to be manipulated in order to achieve particles of the type desired for use according to the present invention (Ugelstad et al. Adv. Colloid Interface Sci. 13, 101 (1980); Ugelstad et al. J. Polym. Sci 72, 225 (1985) and Ugelstad et al Makromol. Chem. Suppl. 10/11, 215 (1985)). These particles are generally 1-100 μm in diameter and may have a standard deviation in diameter of around 1% (i.e. less than 2%).

The formulation will typically contain 25-70% particles, by volume, preferably 35-50%, more preferably 40-45%.

The particles are preferably 0.05 to 4 or 5 mm in diameter, more preferably 0.2 to 1 mm in diameter. Although they may be smaller, e.g. nanoparticles, which may have a diameter of 50 to 10,000 nm e.g. 100 to 1000 nm. The preferred diameter of the particle is dependent on the diameter (width) of the fracture to be plugged, for example a fracture of 13 mm is well plugged by particles 0.5 mm in diameter. Tracers can be used to give information about fracture width in a matrix. The particles in any given formulation will usually be substantially uniform, in so far as the production method allows. The particles are preferably substantially spherical when not compressed. Particles of 0.2 to 0.5 mm in diameter will be preferred in some applications.

The particles of the invention are preferably deformable under pressure (as opposed, for example, to rock particles which are not deformable), this assists in their ability to pack together and to plug the reservoir through forces exerted through the packed particles and against the walls of the fracture. In particular, particles greater than 0.1 mm in diameter will generally be deformable. The particle based plug may leak water until deformation into an oval shape and packing results in a substantially complete seal of the fracture/channel. Thus, "deformable" will be understood in the context of the invention in terms of the ability to form a plug down-hole when packed and to withstand the kinds of pressures disclosed herein. The particles may have a core which is hard, essentially not deformable, but the outer layer is deformable, e.g. the outer 10-30%, e.g. 20%. As described herein, that may conveniently be achieved by pre-softening of wooden particles or by a layered design to the production of Ugelstad particles.

As described elsewhere herein, the particles are generally substantially uniform in size and are typically about as high as they are wide, so spherical or substantially spherical or cuboid, e.g. cuboid with rounded corners, preferably spherical or substantially spherical. 'Diameter' will be understood with these particle shapes in mind.

It may be desirable, for example when plugging fractures greater than 1 mm, in particular greater than 2 or 3 mm wide, to use two different types of solid particles. The first type have a diameter greater than 0.05 mm, typically greater than 0.1 or 0.2 mm, and are deformable. Preferably they have a density similar to that of water (fresh water or sea water—salinity 35 g/L), e.g. a density which is 80-120% of the density of pure water, preferably 90-110%. Such particles are preferably made of wood and have the associated characteristics described elsewhere herein. As described elsewhere herein, the particles are generally substantially uniform in size and are typically about as high as they are wide, so spherical or substantially spherical or cuboid, e.g. cuboid with rounded corners, preferably spherical or substantially spherical. The particles are typically less than 5 mm, preferably less than 3 mm in diameter.

The second type of particle, which may be introduced into the reservoir after the first type, but which are preferably introduced at the same time, are smaller. They are at least four times smaller than the first particle type, preferably at least 5 times smaller than the first particle type, e.g. 5-30 or 10-20 times smaller. These particles may be deformable but need not be, so sand may be used for these particles. Preferably they have a density similar to that of water (fresh water or sea water—salinity 35 g/L), e.g. a density which is 80-120% of the density of pure water, preferably 90-110%. Again, preferably the particles are generally substantially uniform in size and are typically about as high as they are wide, so spherical or substantially spherical or cuboid, e.g. cuboid with rounded corners, preferably spherical or substantially spherical. These particles are typically smaller than 0.2 mm, preferably smaller than 0.05 mm, most preferably smaller than 0.025 mm in diameter and may preferably be Ugelstad particles. These particles are typically greater than 1 μm in diameter.

Alternatively a single population of small particles may be used to form a plug. These are smaller than 0.1 mm, preferably smaller than 0.05 mm, e.g. 1 μm to 50 μm in diameter. These particles are preferably deformable but need not be. The particles are generally substantially uniform in size and are typically about as high as they are wide, so spherical or substantially spherical or cuboid, e.g. cuboid with rounded corners, preferably spherical or substantially spherical. Preferably these are Ugelstad particles.

Alternatively, a single population of very small solid particles may be employed in the form of a colloid, typically these particles are 1-1000 nm in diameter but possibly are even smaller. The particles are dispersed within the viscosifier (which is the continuous phase). Degradation of the viscosifier causes packing of the dispersed solid particles and the formation of a plug, as described elsewhere herein. Colloids may be particularly suitable when plugging in sandstone reservoirs.

A population or "type" of solid particles consists of substantially identical particles and thus within a formulation a first population of particles of one size may be provided together with a second population which is at least 3, preferably at least 5 times larger. Size is generally considered in terms of diameter. A formulation may contain more than two populations of solid particles but will typically comprise only one or two populations.

In carbonate reservoirs fractures exist of varying width. With knowledge of the dimensions of the fracture, the length of the plug which it is intended to make can be estimated and a suitable volume of the formulation of the invention injected into the reservoir. The plugging is essentially achieved because of friction between the particles and the walls and between the particles themselves; the inventor has found that a longer plug (in the flooding direction) is able to withstand greater pressures.

The present invention is also suitable for use in plugging sandstone reservoirs and more specifically the water channels found therein and the same principles apply. Connected pore channels within the sandstone may be blocked to form a plug. Also, there may be microscopic fractures close to the injection well, blocking of these fractures will improve sweep efficiency.

As described in more detail in the Examples, the particles may be generated by standard slurrification processes. This may result in saturation of the particles, which is desirable to equalize their buoyancy with water, as the reservoir environment is largely aqueous. The slurrification process also allows for particles of a homogenous and known size to be generated, in particular to control the maximum diameter of the particles.

Particles of the invention are preferably soakable so that they can have a density approximately (e.g. within 10%, preferably within 5% of the density of pure water) the same as water after they have been submerged. Alternatively they are manufactured to have a density approximately (e.g. within 10%, preferably within 5% of the density of pure water) the same as water if they are not able to absorb water. The formulation is preferably aqueous and the particles are preferably saturated. Depending on whether salt or fresh water is used in the formulation the density of the particles can be adjusted slightly to allow for the higher density of salt/sea water.

More generally the buoyancy/density of the particles is similar to that of the water (fresh water or sea water, salinity 35 g/L) e.g. a density which is 80-120% of the density of pure water, preferably 90-110%. The formulation is aqueous and it is desirable to have approximate equilibrium in density between the solid particles and the rest of the formulation (which is largely viscosifier plus water) so that the particles neither float to the top of the formulation or sink to the bottom. Equalization avoids that and makes flow through the reservoir effective, even at lower flow rates (e.g. at about 1 m per day down-hole).

The particles preferably do not have a smooth surface, this enhances their plugging capabilities. Without wishing to be bound by theory, this enhanced plugging may be due to increased friction of the particles. In some preferred embodiments, the particles have a surface with microscopic hair-like structures. This roughening of the particle surface may be achieved by acid treatment, e.g. by exposing to hydrochloric acid for several hours or even days (e.g. at least 10 hours). Alternative treatment processes include the kraft process (using sodium hydroxide and sodium sulfide); the soda process ("soda pumping" using sodium hydroxide); steam explosion processes, which may use acidic steam; and enzymatic decomposition or by degradation by microorganisms. With wood or wood derived particles, these processes remove some of the lignin found in the cell wall and make holes, this exposes the cellulose fibres. This makes the particles themselves available to be degraded by the preferred microorganisms in the formulation resulting in further roughening of their surface in the reservoir. In this way tendency to form a plug can be enhanced while the formulation is within the reservoir and after it has reached the zone of interest. Excessive degradation of the particles can be controlled by cutting off the supply of other essential nutrients to the microorganisms, other nutrients can otherwise be supplied in the injection liquid.

Injection liquid is usually fresh water or salt water that is injected into the reservoir through an injection well. Salt water can include fresh water to which salts are added, a mixture of sea water and fresh water, natural brackish water and undiluted sea water. The injection liquid can be degassed, supplemented with biocides or exposed to radiation in order to reduce the number of microorganisms in the injection liquid. Preferably the injection liquid is less saline than sea water, the salinity may be 3.5-6%, or less than 4%, possibly less than 3%. Injection liquid may contain nutrients, e.g. a growth medium for the microorganisms.

The growth medium in the formulation of the invention is intended to support the growth of the microorganisms within the formulation, although an adequate carbon source may be provided by the viscosifier. It can contain one or more suitable nitrogen sources, phosphorus sources, potassium sources and trace element sources and vitamins, such as are known in the field. Suitable components of the growth medium, including salts and minerals, are described in the Examples, in particular in Freier medium which represents a suitable growth medium. Further qualities of growth medium can be added to the injection liquid in order to supply the microorganisms in the formulation with additional nutrients. Nutrients may include further sources of carbon but preferably will not.

The viscosifier may provide the necessary physical matrix to hold the formulation of the invention together, i.e. act as a binder or carrier for the solid particles and microorganisms, allowing the slug to remain intact as it transports the particles. The use of viscosifiers, in particular cellulose based viscosifiers, is well known to the skilled man, for example to enhance movement of drilling cuttings by a slurrification process. In some embodiments, the formulation may also comprise a cross-linker which helps to hold the solid particles and bacteria together and eases flow of the formulation to the plugging site. The cross-linker may also be degradable by the bacteria and will typically cross-link molecules of the viscosifier. Alternatively, molecules of the viscosifier, such as polysaccharide chains e.g. CMC chains, may be cross-linked without the need for an additional cross-linker component as such. Cross-linking may be achieved, for example, using a polyamine, chloromethypyridylium iodide or by irradiation. Suitable methods for cross-linking cellulose and cellulose derivatives are described in U.S. Pat. Nos. 5,304,620 and 6,734,298.

The viscosifier is typically either soluble in water or forms a suspension therein. On a weight by weight basis, the viscosifier may be present in solution/suspension (typically with water or brine) at 150-10000 ppm, more usually 300-5000 ppm.

Viscosifiers are preferably polysaccharides and cellulose and derivatives thereof are especially preferred. Such derivatives include polymers of glucopyranose monomers in which some or all (usually some) of the hydroxyl groups —OH have been substituted by groups —OR in which R may be, for example, an alkyl, hydroxyalkyl or carboxylic acid moiety, typically the R groups are $C_{1-5}$ groups with $C_{1-3}$ being preferred. Derivatives incorporating carboxylic acid moieties may exist in salt form, e.g. sodium carboxymethyl cellulose. Preferred examples of cellulose derivatives include carboxymethyl cellulose (CMC), polyanionic celluloses generally, methyl cellulose or hydroxypropyl cellulose, hydroxyethyl cellulose, ethyl cellulose, nitrocellulose, hydroxyethyl methylcellulose and hydroxypropyl methylcellulose. With CMC and other similar cellulose derivatives, typically no additional cross-linker is required.

Cellulose derivatives such as CMC and other polyanionic celluloses vary in chain length and degree of substitution of the glucopyranose monomers. CMC molecules are somewhat shorter, on average, than native cellulose with uneven derivatization giving areas of high and low substitution. This substitution is mostly 2-O- and 6-O-linked, but may also be 2,6-di-O-, 3-O-, 3,6-di-O-, 2,3-di-O- or 2,3,6-tri-O-.linked. It appears that the substitution process is a slightly cooperative (within residues) rather than random process, giving slightly higher than expected unsubstituted and trisubstituted areas. CMC molecules are most extended (rod-like) at low concentrations but at higher concentrations the molecules overlap and coil up and then, at high concentrations, entangle to become a thermoreversible gel. Increasing ionic strength and reducing pH both decrease the viscosity as they cause the polymer to become more coiled.

Suitable polyanionic cellulose viscosifiers have the CAS number 9004-32-4, e.g. as supplied by Kelco Oil Field Group under the trade names CELPOL®R, CELPOL®SLX and CELPOL®RX.

A further preferred cellulose polymer is Exilva, a micro-bifrillated cellulose which has higher than typical numbers of accessible hydroxyl groups resulting in high water retention capability. This product forms a suspension in water and it is advisable to mix thoroughly after dilution to ensure the fibrils are well separated and the product does not settle. A water-soluble polymer such as CMC, xanthan gum or guar may be employed to stabilise the Exilva suspension. This product is available from Borregaard, Norway.

Other suitable polysaccharide viscosifiers are gums, such as are produced by microorganisms, e.g. diutan gum and xanthan gum. Suitable gums are identified by their CAS numbers, CAS 11138-66-2, 125005-87-0 and 595585-15-2, e.g. GEOVIS®XT and XANVIS® supplied by the Kelco Oil Field Group. Suitable bacteria to degrade xanthan and other gums are known in the art, e.g. *Peanibacillus alginolyticus* XL-1, *Verrucomicrobium* sp. GD, *Bacillus* sp. GL1, *Bacillus* sp. YJ1, *Cornynebacterium*. Xanthan may first be degraded to acetate and propionate, sulphate reducing bacteria (SRB) may then be employed to further metabolise these xanthan breakdown products.

As previously mentioned, preferred microorganisms in the formulation can degrade cellulose derivatives to form disaccharides and eventually hydrogen, carbon dioxide, ethanol, acetate and lactate. It is degradation of the viscosifier which causes the shift from a flowable suspension to a solid plug of packed particles. This relationship between the enzymatic capabilities of the microorganism and the viscosifier is central to the present invention.

Freier-medium is a particularly suitable source for providing the salts and minerals of the growth medium. The viscosifier, e.g. CMC, is the sole or main carbon source in the formulation. The growth medium (together with the viscosifier) serves to support microbial growth for long enough to achieve breakdown of the viscosifier and conversion from flowable suspension (slug) to solid plug. Freier-medium but with CMC as the carbon source provides a suitable viscosifier plus growth medium mixture.

The viscosifier must be suitable as a viscosifier in a hydrocarbon reservoir environment and act as a carbon source for the microorganisms. The role of viscosifiers is well known in the field of oil recovery and here this component must, in particular, act as a lubricant allowing the formulation in the form of a slug to move through the reservoir. When present the viscosifier provides a high viscosity environment but the formulation is mobile within the reservoir. When it has been degraded the viscosity of the formulation is reduced (e.g. to a viscosity similar to water) but friction between the particles themselves and between the particles and the matrix walls is increased such that plugging can take place.

The viscosifier will preferably provide the formulation with a viscosity of at least 2 cP, e.g. 5-15 cP, preferably about 10 cP when it is introduced downhole but may be higher, e.g. at least 5 or 10 cP, possibly more than 15 or 20 cP. At this viscosity the formulation can transport the particles, microorganisms and any additional growth media through the fractures. When the microorganisms have broken down the viscosifier, the viscosity of the formulation decreases, for example to less than 3 or 2 cP, preferably about 1 cP; this will result in the formation of a solid plug (water has a viscosity of 1 cP at 20° C.).

In a further aspect, the invention provides a plug formed in a hydrocarbon reservoir, said plug comprising solid particles as defined herein and optionally microorganisms as defined herein, optionally in the form of spores.

As an alternative to microorganisms in the formulation, it may be desirable to use enzymes which are capable of digesting the viscosifier. The enzymes are typically saccharolytic or lignocellulolytic enzymes, preferably enzymes which can digest cellulose, including cellulose derivatives such as carboxymethyl cellulose. Such enzymes are known generally as cellulases and are capable of hydrolysing the 1,4-beta-D-glycosidic linkage found, inter alia, in cellulose and hemicellulose. The enzymes may tolerate different conditions as compared to the microorganisms, in particular they may tolerate higher temperatures which may make them preferred for certain reservoirs. They may also be active at more extremes of salinity, pressure etc.

Thus, in a further aspect, the present invention provides a formulation comprising:
(a) a cell-free enzyme;
(b) solid particles, preferably made from wood or other cellulosic material; and
(c) a viscosifier which is a substrate for the cell free enzyme of (a).

In a further aspect the present invention provides a formulation comprising:
(a) microorganisms or cell-free enzymes;
(b) solid particles made from wood or a wood derived product; and
(c) a viscosifier which is a substrate for the microorganisms or cell-free enzymes of (a).

In the above formulations, the enzyme(s) is present in purified or partially purified form, in other words not associated with living cells (not intracellular or bound to an intact cell membrane or cell wall).

The particles and viscosifier are as discussed above in the context of formulations comprising microorganisms.

Suitable enzymes are produced by fungi, bacteria and protozoans and the enzymes may be from or derived from bacteria which are themselves of use in formulations of the invention, e.g. *Clostridium thermocellum*, preferably the strain JW20. In preferred embodiments more than 1 enzyme will be included in the formulation, e.g. 2-4 enzymes that act to degrade cellulosic material.

In some embodiments a cellulase may be provided as part of a multi-enzyme complex known as a cellulosome. Cellulosomes are produced by many cellulolytic microorganisms, e.g. *C. thermocellum, C. cellulolyticum* and *C. cellulovorans*.

Suitable cellulases which may be used individually, together or as part of a cellulosome include: endocellulases, exocellulases or cellobiohydrolases, cellobiases or beta-glucosidases, oxidative cellulases or cellulose phosphorylases. Examples include endo-1,4-beta-D-glucanase (beta-1,4-glucanase, beta-1,4-endoglucan hydrolase, endoglucanase D, 1,4-(1,3,1,4)-beta-D-glucan 4-glucanohydrolase), carboxymethyl cellulase (CMCase), avicelase, celludextrinase, cellulase A, cellulosin AP, alkali cellulase, cellulose A 3, 9.5 cellulase, and pancellase SS. A CMCase is particularly preferred.

Suitable enzymes will be catalytic in downhole conditions, in particular the enzymes themselves can be considered thermophilic, or even hyperthermophilic. For example tolerating temperatures in excess of 70° C., preferably in excess of 80 or 90° C., optionally in excess of 100° C. Naturally occurring enzymes which have been modified to adapt them to downhole conditions may be used.

In a further aspect, the present invention provides a method of treating a hydrocarbon reservoir in order to prepare it for recovery of hydrocarbons therefrom, which method comprises introducing into the reservoir a formulation of the invention.

Any hydrocarbon reservoir may be treated according to the present invention but carbonate reservoirs are preferred. Oil containing reservoirs are also preferred.

Alternatively viewed, the present invention provides a method of establishing a plug in a hydrocarbon reservoir, the method comprising introducing into the reservoir a formulation of the invention. The present invention provides a method of establishing a plug in a hydrocarbon reservoir, the method comprising introducing into the reservoir a formulation comprising:
(a) microorganisms or cell-free enzymes;
(b) solid particles; and
(c) a viscosifier which is a substrate for the microorganisms or cell-free enzymes of (a).

These methods may further comprise introducing injection liquid into the reservoir in order to push the formulation to a target region within the reservoir. Preferred features, definitions and so on described above in relation to the solid particles, microorganisms and viscosifier of the formulations of the invention apply also to these methods and components employed therein.

The reservoir is typically one that has previously produced hydrocarbons, and in particular will already have undergone a phase of Enhanced Oil Recovery (EOR). It may be a carbonate or sandstone reservoir. These methods will typically be performed on reservoirs which have already been flooded with an injection liquid, e.g. water. Injection liquid will also generally be added after the introduction of the formulation in order to push the flowable formulation into the reservoir. The injection liquid may contain nutrients for the bacteria within the formulation, e.g. phosphates and other salts, vitamins and minerals and optionally further sources of carbon for the bacteria, e.g. cellulose, CMC or cellobiose.

In preferred embodiments plugging is achieved without having to introduce additional nutrients, in particular a carbon source, for the microorganisms. In other words, it is not necessary to maintain the plug by providing an on-going supply of nutrients, because the plugging is achieved by the solid particles, not biomass.

Thus the methods of the invention preferably comprise the following steps:
(i) introducing into the reservoir a formulation of the invention; and
(ii) introducing injection liquid into the reservoir in order to push the formulation to a target region within the reservoir.

In a typical reservoir set up, injection liquid flows from the injection well, through the reservoir and exits (or partially exits) through the production well. Of course, the desire is that the injection liquid will also force oil from the reservoir to the production well.

The target region within the reservoir is the region where it is desired to form a plug. This may be a specific area, e.g. at a certain distance within the flow channels, where modelling or other studies have taken place but need not be and the target region may only be understood in very general terms. The pressure generated by injection of liquid forces the formulation, which may be in the form of a suspension, into the reservoir along flow channels, e.g. fractures in a carbonate reservoir. As the viscosifier is degraded, the formulation develops a reduced ability to flow and this resistance builds until the flow channel/fracture is blocked; the particles are forced in the flow direction and a plug forms of packed particles.

Generally the plugging process will block the larger, dominant fractures or channels first (the most dominant waterways transport the largest volume of water and will thus carry the dominant slug of particles) and this would result in a new flooding pattern where new fractures or channels became dominant, this process could take about 1 to 2 weeks. Then the process could be repeated to target the new dominant fractures or channels. The process could be repeated several times, as required, in order to cause sufficient blocking to increase oil production.

Generally the larger the fracture the larger the particle size required for effective blocking, e.g. a 13 mm wide fracture may be most effectively blocked using particles of 0.5 mm diameter and so as the process is repeated, the size of the particles introduced will typically be reduced with successive applications. In general, the diameter of the particles will be 1-10% of the width of the fracture, preferably 3-8%, but may be greater, e.g. up to 30 or 20% of the width.

By the introduction of plugs (e.g. plugs in dominant and less dominant fractures or channels) in the matrix, it is possible to force injection liquid into new zones and therefore not just reverse the decline in sweep efficiency but change the shape of the sweep zone to access and recover oil from new areas.

Through understanding of flow rate through the reservoir from injection well to production well, the positioning of the plug may be controlled. The change from flowable slug to solid plug may be initiated or enhanced by shutting off the injection of liquid or increasing or decreasing the flow thereof.

As has been described herein, key to the present invention is the transition from a mobile liquid in which a viscosifier carries solid particles to a pluggable mass of solid particles. This transition occurs through degradation of the viscosifier which, as discussed herein, may be achieved by microorganisms or enzymatic degradation. However, the principle is more general and thus, in a further aspect, the present invention provides a method of establishing a plug in a hydrocarbon reservoir, the method comprising introducing into the reservoir a formulation comprising a viscosifier as defined herein and solid particles as defined herein and then reducing the viscosity of said viscosifier, thereby causing said solid particles to form a plug within said hydrocarbon reservoir. Unless otherwise clear in context, preferred and additional features of the earlier described aspects of the invention also apply to this aspect. For example, this aspect of the invention may conveniently involve a step of introducing injection liquid into the reservoir in order to push the formulation to a target region within the reservoir prior to reducing the viscosity of the viscosifier. Viscosity is typically reduced by degradation of the viscosifier, that is conversion from a high molecular weight polymer to low molecular weight molecules which have a viscosity similar to water and are no longer able to prevent packing of the solid particles to form a plug. As in all aspects, when introduced into the reservoir the viscosifier is able to transport the solid particles, but once degraded, flow of the solid particles ceases and plugging takes place.

Without wishing to be bound by theory, it is believed that degradation of the viscosifier will begin in the front section of the slug and so plugging starts at the front end. At this stage the slug/plug is still permeable to water but particles are accumulating and condensing from the front and extending backwards causing an increase in backpressure. The backpressure forces the rear of the slug against the more solid front portion. Over time the slug transforms into a mass of particles and is no longer significantly water permeable. The particles may constitute about 40-45% of the total volume of the slug and so the length of the slug will decrease as the viscosifier is degraded and a compacted plug forms. The plug then functions as a check valve.

The purpose of the plug is to allow a pressure differential to build up across it, thereby forcing injection liquid out of the flow channel and into the matrix, forcing oil out of the matrix. The plugs according to the present invention may withstand a pressure differential of at least 2000 PSI, preferably at least 4000 PSI, more preferably at least 6000 PSI. As discussed elsewhere herein, the longer the plug in the flooding direction, the higher the pressure differential it can withstand. This relationship is approximately linear. By way of example, the pressure on the injection side of the plug may be around 14,000 PSI and the pressure on the production side of the plug may be around 6,000 PSI.

Plug lengths may be measured in meters, preferred plugs being greater than 5 m, preferably greater than 10 m, more preferably greater than 25 m in length, e.g. 50-100 meters. Generally speaking smaller particles are best suited for longer plug lengths, e.g. a diameter 0.5 mm, preferably 0.2 mm for plug lengths greater than 1.5 m. The distance between the walls of the fracture to be plugged is also relevant, thus if a plug of 10 m or larger is desired, solid particles in the formulation should be 1000 times smaller than the width of the fracture.

The present invention provides a method of oil recovery from a hydrocarbon reservoir, which method comprises introducing injection liquid into said reservoir, the reservoir comprising a plug of solid particles as defined herein, and recovering oil from said reservoir.

The present invention also provides a method of oil recovery from a hydrocarbon reservoir, which method comprises establishing a plug in said reservoir by performing such a method of plug establishment as described herein, introducing injection liquid into said reservoir and recovering oil from said reservoir. As mentioned earlier, injection liquid is used to force oil from the reservoir to the production well and plugging established flow channels can enhance oil recovery by forcing injection liquid into new areas.

The formulation of the invention may conveniently be prepared by mixing the components defined above; thus mixing microorganisms, optionally in spore form, particles and viscosifier, optionally together with a cross-linker and/or growth medium. Water may be added to the mixture and/or the viscosifier may be blended with water and the other components added thereto. Such a method of preparation constitutes a further aspect of the present invention. Mixing of the solid particles into the liquid components may be by slurrification to form a suspension. Temperature and pH of the prepared formulation may be controlled, in particular for transportation of the formulation where it is desired to inhibit degradation of the viscosifier by the microorganisms.

In preferred embodiments, in order to reduce the buoyancy of particles made of wood or similar cellulosic materials, the particles or the material from which they are formed are submerged in order to saturate them. Saturated wood or wood derived particles are preferred. This results in an increase in the density of the particles to be closer to the density of water.

The invention is further described in the following non-limiting Examples and the figures in which.

EXAMPLES

Example 1—Degradation of Carboxymethyl Cellulose by *Clostridium thermocellum*

Bacteria
*Clostridium thermocellum* (CT) JW20; ATCC 31549
Growth Medium
CT were cultured according to the methodology described by Freier et al. in Applied and Environmental Microbiology [1988] vol 54, No. 1, p 204-211 but with carboxymethyl cellulose (CMC) present as the carbon source. The CMC product used was CELPOL®RX, a highly viscous polyanionic cellulose (CAS number 9004-32-4) available from Kelco Oil Field Group.

Specifically, the culture medium contained (per liter of deionized water)

1.5 g $KH_2PO_4$
4.2 g $Na_2HPO_4.12H_2O$
0.5 g $NH_4Cl$
0.5 g $(NH_4)_2SO_4$
0.09 g $MgCl_2.6H_2O$
0.03 g $CaCl_2$
0.5 g $NaHCO_3$
2 g of yeast extract
0.5 ml of vitamin solution. The vitamin solution contained (per liter of distilled water)

40 mg of biotin, 100 mg of p-aminobenzoic acid, 40 mg of folic acid, 100 mg of pantothenic acid calcium salt, 100 mg of nicotinic acid, 2 mg of vitamin B12, 100 mg of thiamine hydrochloride, 200 mg of pyridoxine hydrochloride, 100 mg of thioctic acid, and 10 mg of riboflavin.

5 ml of mineral solution. The mineral solution contained (per liter of distilled water) 1.5 g of nitriloacetic acid, 3 g of $MgSO_4$-$7H_2O$, 0.5 g of $MnSO_4$. $H2O$, 1 g of NaCl, 0.1 g of $FeSO_4$ $7H2O$, 0.1 g of $Co(NO_3)_2.6H_2O$, 0.1 g of $CaCl_2$ (anhydrous), 0.1 g of $ZnSO_4$. $7H_2O$, 50 mg of $NiCl_2$, 10 mg of $CuSO_4*5H_2O$, 10 mg of $AlK_2(SO_4)_3$ (anhydrous), 10 mg of boric acid, 10 mg of $Na_2MoO_4*2H_2O$, 10 mg of $Na_2WO_4$-$2H_2O$, and 1 mg of $Na_2SeO_3$ (anhydrous)

1% carboxymethyl cellulose (CMC).

Growth Experiments

A culture of CT bacteria was inoculated and allowed to grow in a flask containing the above growth medium as described in Freier et al. supra for 5 days (referred to herein as Freier medium).

The Freier approach to CT culturing was modified with bottles containing 3 different fractions of oil. One set of bottles contained 90% of oil, one set of bottles contained 50% of oil and the last set of bottles contained 10% of oil. The remaining liquid contained the Freier medium with CMC at 1%. Bottles containing 100% Freier medium with CMC (1%) were provided as control. The bottles were shaken every 3 hours during the day. The bottles were opened after 1 week.

Ethanol was produced in concentrations corresponding to the volume and concentration of growth medium containing CMC, indicating degradation of CMC.

The oil did not have a inhibiting effect on the culture. The culture does not grow and metabolize within the oily fraction. We concluded that the growth medium was effectively removed in the high concentration of oil due to the fact that oil and water are not soluble. We also concluded that the culture could not utilize hydrocarbons as a carbon source.

Viscosity Test

The media collected after the above degradation was added to a glass cylinder and the time taken for a lead ball to sink through the liquid was measured. The experiment was repeated with pure water in place of the growth medium and with a sample of the growth medium which had not been inoculated with CT.

Media which had been exposed to CT as described above allowed the lead ball to move through it (acceleration, time and maximum velocity) in a similar fashion to the pure water. The media which had not been contacted with CT, on the other hand, offered significant resistance to the passage of the ball.

Using this test it was no longer possible to detect CMC in the sample which had been in contact with CT.

These experiments indicated that most CMC is degraded by CT and that the resultant viscosity is similar to that of pure water.

Example 2—Generation of Wooden Particles

Sandpaper (different grades of sandpaper result in different sized particles) was applied to pieces of wood (*Corylus avellana*) to generate particles of about 200μ, 500μ or 1-2 mm in diameter.

Example 3—Plugging Experiments Using Wooden and Sand Particles

Wood particles of 0.5 mm and 1-2 mm in diameter produced as described in Example 2 were inserted with water into a transparent hose of 15 mm diameter, 150 cm in length with a downstream valve. After filling the hose, a slowly increasing pressure differential was applied by injecting water from one end of the hose to provide a backpressure of 8 bars. The plug was pushed to become more compact and resisted the backpressure until the backpressure reached a maximum. The plug length could be controlled by the volume of particles added and plug lengths of 10 and 15 cm were generated. Before the maximum backpressure was reached the plug started moving in the flow direction, the particles sticking together and the plug gliding along the hose. Shaking the hose tended to release the plug, enabling it to slide further. The larger (1-2 mm) particles allowed a greater flow of water through the plug.

The experiments were repeated with sand particles. These were much less effective at plugging and the particles did not stick together as the plug accelerated through the hose. When a 25 mm plug was generated then there was a plugging effect but it was very easy to release by shaking.

The results of these tests are summarised in Table 1 below.

TABLE 1

| Particle | | | | | | |
|---|---|---|---|---|---|---|
| Quality | Shape | Size (mm) | Hose diam. (mm) | Plug size (mm) | Max Diff Pres. (bar) | Observations |
| Wood particle | Rounded | 0.5 | 15 | 10/15 | 8 | "10": Slip pres. < 8 bar<br>"15": Slip pres. > 8 bar<br>Maintained plug integrity |
| Wood particle | Rounded | 1-2 | 15 | 10/15 | 8 | "10": Slip pres. < 8 bar<br>"15": Slip pres. > 8 bar<br>Maintained plug integrity |
| Sand | Rounded | <1 | 15 | | 8 | No plug integrity up to 25 bar |

Example 4—Acid Treatment of Particles

Particles generated as described in Example 2 were exposed to concentrated hydrochloric acid for 15 hours and then an alkaline wash was used to increase the pH and establish a stable pH of about 7. Water alone could be used to remove the acid.

The particles were added to Freier medium as described in Example 1 but with no carbon source (CMC absent) and contacted with CT. The bacteria attacked and partially degraded the particle.

The particles were studied under a microscope. The treated particles were much more deformed and "hairy" or "fluffy" in appearance than those which were not acid treated.

The cell walls of wood have lignin and cellulose. The above acid treatment attacks the lignin layer making the cellulose parts accessible to degradation by cellulolytic bacteria such as CT.

Example 5—Industrial Scale Production of Particles

Slurrification machinery (National Oil Well Slurrification Unit) used in oil drilling to process coarse cuttings can be used to process wood to generate particles suitable for use in the present invention. The wood is run through a mill with water under high pressure and after about 10 minutes the suspension is forced through a mesh of the desired size. These mesh filters effectively size the particles with the larger particles which cannot pass through the filter being recycled for further milling. The resultant particles can be as small as 200µ in diameter. The particles are adequately uniform and solid but saturated.

Example 6—In Situ Set Up

Features of Exemplary Carbonate Hydrocarbon Reservoir:

| | |
|---|---|
| Volume of fracture | 100 barrels (1 m³ = 6.29 barrels) |
| Length from injection well to production well: | 2000 feet |
| Volume of injection liquid: | 20000 barrels per day |
| Flow rate: | 30 min |
| Differential pressure max: | 6000 PSI |
| Expected width in fractured structure: | 1-5 mm |

The flow rate is the time taken for liquid to pass through the reservoir from injection well to production well. This example reservoir which may be treated according to the invention exhibits an extreme flow rate indicative of an extensive system of well developed fractures.

The differential pressure maximum is the maximum pressure differential that it is desired generate across the plug.

If required the fractures can be pre-treated by hydrochloric acid to increase the resistance of the fracture walls, i.e. to increase the potential for friction.

The suspension of particles, bacteria etc. is injected into the injection well system. This is hydraulically forced further into the fracture system by back pressuring with injection water. The suspension will displace all alkaline water.

The bacteria attack any pure cellulose and the carboxymethyl cellulose within the suspension. The cellulose inside the particles is only degraded if the particles are pre-treated for the purpose.

Example 7—Further Tests to Study Plugging Effects in Sandpacks and Hoses

Ceramic Particles:

Long transparent hoses of 13 mm diameter were used as equivalents to a magnified connected pore system. Particles of different sizes where flooded through the hoses as slugs to observe if the particles were able to form plugs. The particles were of same size and same shape and were of solid ceramics. The volume of particles introduced was equivalent to an 8 cm long plug. The test system was capable of supporting a backpressure to the plug of 15 Bars.

Particles of the following size and shape were tested:

| |
|---|
| 1. Ø < 0.5 mm |
| 2. Ø = 1-2 mm |
| 3. Ø > 5 mm |

Observations:

No plugs formed.

Wooden Particles:

The same test was performed with water-soaked particles of the same shape size and shape made of wood—Spruce. No formation of plug was observed of particles sized Ø<0.5 mm and Ø>5 mm. However plugs were formed by use of particles sized Ø=1-2 mm. The plug was flushed out of the hose by a backpressure exceeding 8 bars.

All the tests including the non-plugging tests were repeated 10 times and showed the same results.

Test to Understand the Mechanisms by which the Wooden Particles Plugged:

Similar test setups as described above were performed using the wooden particles. The structure of the particles were studied through the transparent hose showing that the particles deformed slightly, they were originally round shaped and soaked by water.

The backpressure led to the wooden particles forming an oval shape with a slightly soft surface.

Comparing the surface of ceramic particles to the surface of the wood particles clearly revealed the potential for higher surface friction on the wood particles. Studying the surface of the wood particles with a microscope revealed small fiber threads more or less as hair on the surface of the particle, while the ceramic particle was smooth.

Thus effective plugging is dependent on the particle diameter (relative to the diameter of the hose/fracture), deformability and the surface friction of the particles.

Sandpack Test

A sandpack, 10 cm in length, 5 cm in diameter containing grains of 1 mm diameter was set up and soaked wooden particles of 0.05 mm diameter were added. The particle size was selected in correlation to the relative size of the pore mouth. Pores are formed as a series of interconnecting voids between the particles, the size of the pores and thus the pore mouth being dependent on the size/diameter of the grains. The system was first flooded with water and after flooding, particles were added to the water. The particles blocked the pores immediately, i.e. did not enter the pack and form a plug.

A further test was performed using a sandpack of larger diameter and pebbles of 10-17 mm in size. These pebbles formed an enlarged pore system generating a channel through the sandpack. Sand was packed around the pebbles to provide a single channel through the sandpack.

Flooding was initiated with a viscosity 10 cP and the particles flooded through the system. A series of floodings with different viscosities were performed (reduced by 2 cP per flooding). The system started to plug when flooded with viscosity below 4 cP. The agent used to control viscosity was Carboxyl Methyl Cellulose (CMC) dissolved in the water.

Example 8—Testing Viscosity Reduction

*Clostridium thermocellum* JW20 represents an example bacteria which has enzymatic capabilities to degrade Carboxyl Methyl Cellulose CMC and Poly Anionic Cellulose (PAC). A product of CMC was used to viscosify the carrierfluid. 5% was added to bring up viscosity of the water to 10 cP. Before adding CMC to the water a solution of nutrients equivalent to 1% Vol was added to the water. The nutrients is a defined composition based on the Freier-Medium in which the cellobiose is replaced with CMC 1:1 Vol %:Vol %.

Viscosity measurements shows that the viscosity of the fluid is altered from 10 cP to 1.5 cP.

Example 9—Blocking Connected Pore Systems

A test was set up equivalent to the Sandpack test of Example 7 and flooded with the carrier fluid including modified Freier media with CMC, CT and wooden particles at 35% Vol of the liquid. The composition was injected into the sandpack and shut in for 2 weeks. The system was flooded with pure water, the injection pressure had to be elevated to 12 bars to resume flooding through the system. When opening the Sandpack it was observed that the particles were blocking the connected pore systems.

The test demonstrates that it is possible to introduce particles into the sandpack via the injection water, transport and permanently locate them. This operation is possible where a viscous fluid can transport the particles and where the viscosity can be reduced by microbial activity thereby aggregating particles in the pores. An operation of this kind reduces permeability dramatically in the sandpack.

Example 9—Investigating Plug Length

A test set up as first described in Example 7 was prepared using wooden particles of 1-2 mm and the same results were observed. Then the plug length was increased to 15 cm and a backpressure of 15 Bars was exceeded before the plug was forced out of the hose (the test was repeated 6 times with the same result).

Example 10—Testing a Different Shaped Hose

The test described in Example 7 was repeated using a 100 cm hose with a 5 cm diameter that has been reshaped to be an oval (width 1.3 cm and height 7.15 cm). Plugging was shown under the same circumstances as seen in Example 7.

Example 11—Chalk Fracture Experiment

Figure 2:
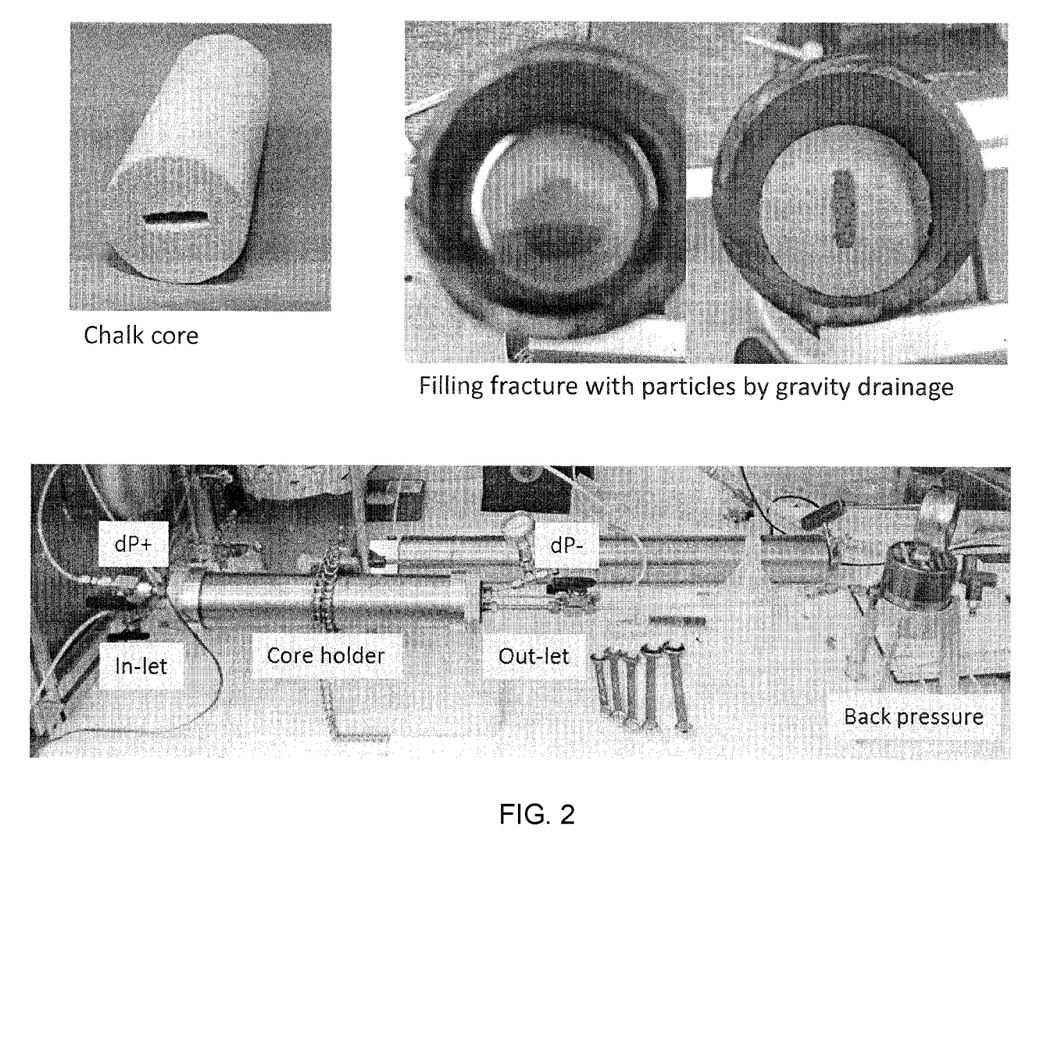
FIG. 2—shows the set-up of experiments performed in a modelled chalk fracture. These experiments are outlined in Example 11 and demonstrated increased pressure produced in the chalk fracture as a consequence of the formation of a plug of wooden particles. The experiments also demonstrated facilitated movement of wooden particles through the chalk fracture when said particles were suspended in a viscosifier (xanthan).

An artificial fracture was created in natural Austin Chalk (see FIG. 2). Wooden particles of 1 mm diameter in water only (no viscosifier) were flowed through the fracture and formed a plug immediately at the inlet over the first 10 cm of the fracture.

Figure 3:
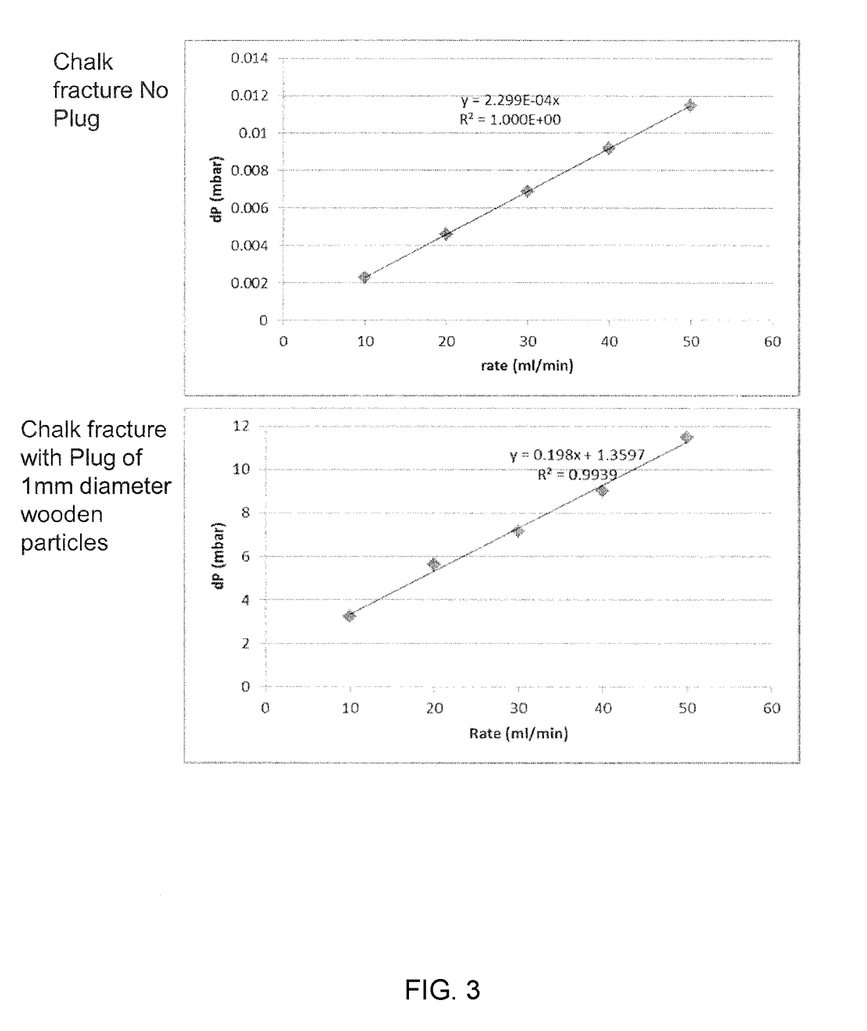
FIG. 3—shows graphs describing pressure (mbar) vs rate of flow of water (ml/min) through the model chalk fracture in the absence of a plug (top graph) and with a plug formed of 1 mm diameter round wooden particles (bottom graph). A mobility reduction factor (MRF) of 861 was achieved upon formation of the wooden plug.

Reduction of particle mobility and pressure build up upon plug formation in the chalk core was measured (see FIG. 3). The differential pressure in the fracture before the plug was generated was 0.00023 mbar and after plug formation was 0.19803 mbar equaling a mobility reduction factor of 861 (see FIG. 3).

In order to demonstrate the ability of a viscosifier to facilitate transport of wooden particles to fracture sites distant from the site of injection, an experiment was performed in the same fractured chalk comparing 1 mm diameter particles suspended in water and the viscosifier xanthan. The viscosity of the water containing the 1 mm wooden particles was increased to 2000 centipoise by the addition of xanthan. When the resultant suspension was introduced into the chalk fracture the particles were able to move through the fracture relatively unimpeded. This demonstrates the ability of a viscosifier to facilitate movement of plugging particles to sites remote from the injection well in a chalk fracture.

Example 12—Buoyancy of Wooden Particles

In order to adjust the buoyancy of wooden particles for optimum suspension at different viscosities, the particles may be soaked in water or brine.

Wood particles are filled into a pressure cylinder containing brine. Pressure is increased at a rate of 2 bar/hour up to a desired pressure, typically between 2 and 20 bar. The particles are kept at the given pressure for minimum 2 days, maximum 1 week. Pressure is then reduced to atmospheric pressure over a time period of 1 hour. The composition of brine, the absolute pressure and the pressure exposure period is varied to adjust wood particle density.

In one particular example, 50 g of wood particles were filled into a 200 ml stainless steel pressure cylinder. Pressure was increased by injecting brine at constant pressure step wise until reaching 20 bar. The pressure was increased at a rate of 2 bar/hour. Pressure was maintained by injection pump at 20 bar for 1 week. Pressure was then released with a gradient of 20 bar/hour to atmospheric pressure.

Example 13

A) Degradation of Xanthan by Anaerobic Xanthan-Degrading Bacteria

Figure 4:
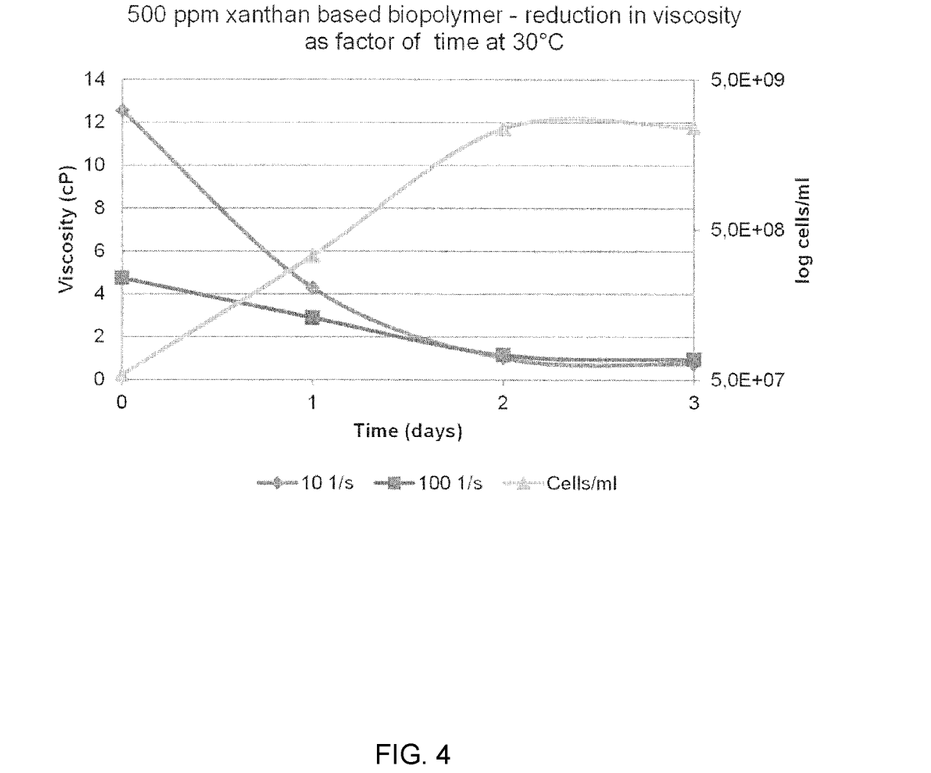
FIG. 4—is a graph showing the reduction of xanthan viscosity over the course of three days when xanthan is incubated at 30° C. in anoxic conditions with an anaerobic xanthan degrading bacteria. A concomitant increase in bacterial cell growth is observed as the xanthan is degraded.

A microbial system for degradation of the viscosity of a slug has been established. The slug consists of a xanthan based biopolymer, anaerobic xanthan-degrading bacteria and surplus of mineral nutrients, trace elements, vitamins and nitrate. The microbes operated optimally at mesophilic conditions (20-30° C.) and sea water salinity. In a test system with 500 ppm xanthan biopolymer, a complete degradation of viscosity was observed within 2 days (FIG. 4). The concomitant increase in cell number verifies that the biopolymer was utilized for anaerobic growth of the bacteria. The degradation time of the slug may be optimized for different biopolymer concentrations by adjusting the initial cell number and essential nutrients in the slug.

B) Degradation of Exilva (Cellulose) by *Clostridium thermocellum*

Figure 5:
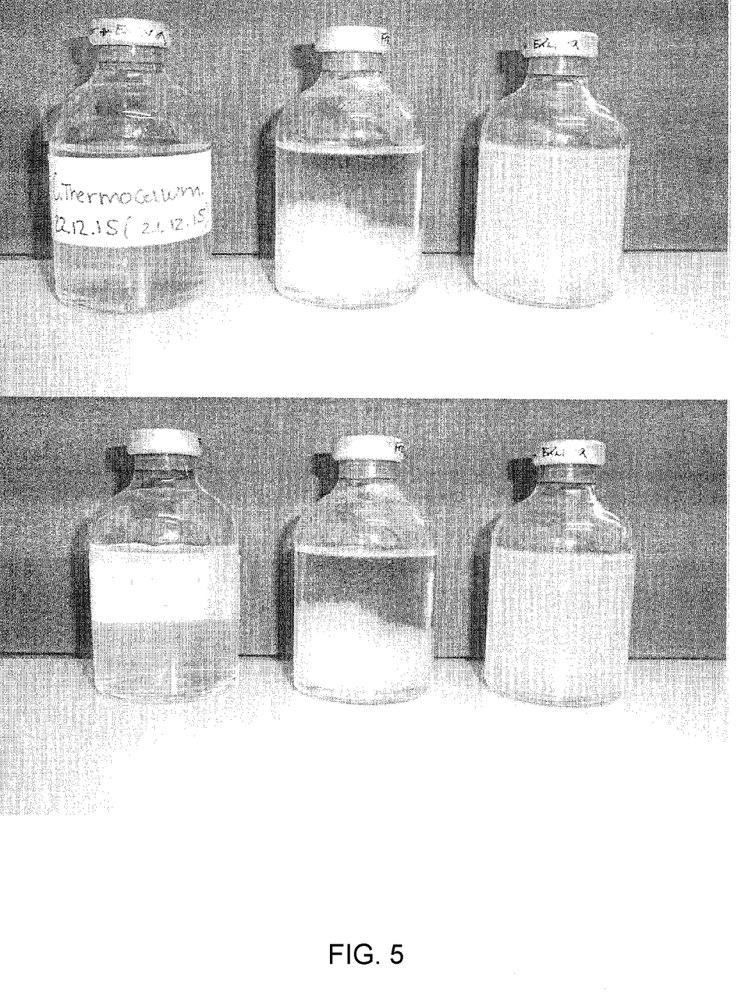
FIG. 5—shows that the turbidity of Exilva (microfibrillated cellulose) is decreased (correlating with decreased viscosity) when incubated with *Clostridium thermocellum* (CT). Bottles from left-right show Exilva+CT, Exilva (settled) and Exilva dispersed.

*Clostridium thermocellum* is able to degrade the microfibrillated cellulose polymer product named Exilva. Exilva is visible in the growth medium as a turbid phase at the start of incubation. As degradation occurs, the turbidity decreases and finally leaves the growth medium clear at end of the growth phase (FIG. 5).

Example 14—Two Component Plug

In certain circumstances plugging of fractures may be optimised by use of a two component plug comprising particles of a larger size in combination with smaller particles which are capable of filling the void space between the larger particles, thus decreasing permeability of the plug. Previous results showed that a plug consisting of the 1 mm round wood particles gave a MRF value of 700-1100. However, the permeability of such plug may be further reduced by the injection of a second slug of smaller particles (smaller wood particles 0.2 mm in diameter (seived)) which are introduced to fill the void space between the larger 1 mm round wood particles.

In order to demonstrate this principle the following experiment was performed.

Figure 6:
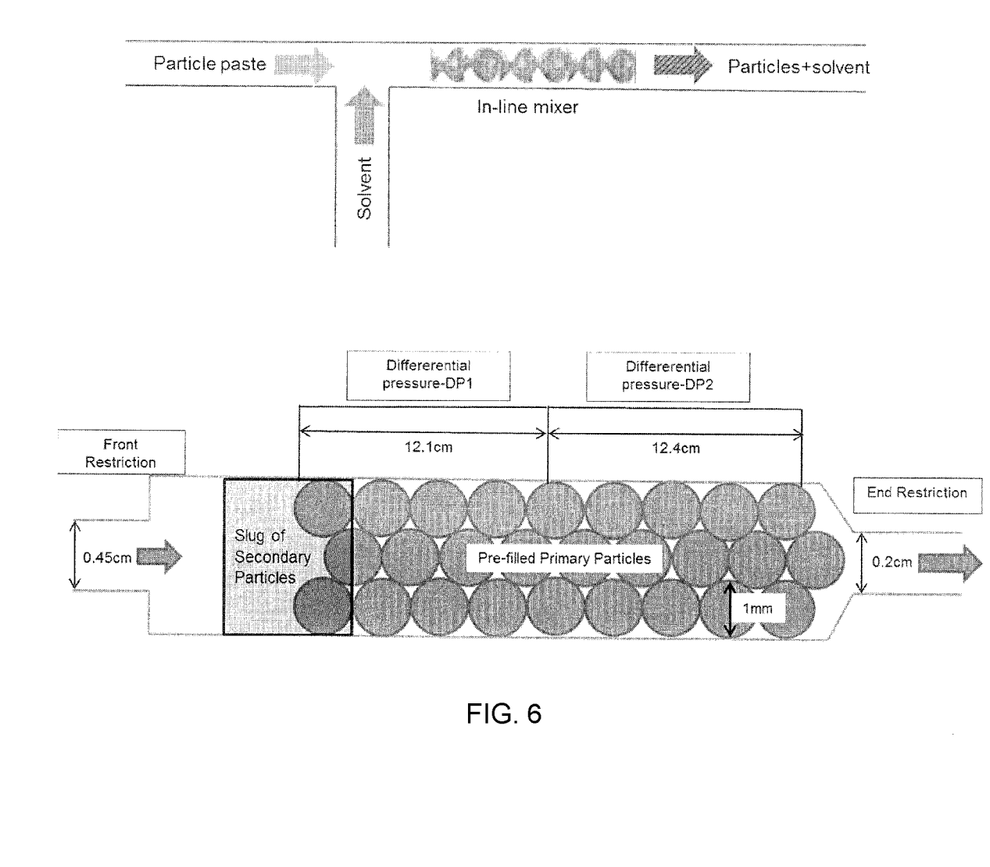
FIG. 6—is a schematic representation of apparatus for a two component plug experiment (described in Example 14). The top image is a schematic drawing of the particle and solvent (viscosifier) inlet. This inlet set up allows the viscosifier to wooden particle paste ratio to be adjusted easily during the course of the experiment. The bottom image is a schematic diagram of the experimental set up for investigating the formation of a two component plug consisting of larger particles interspersed with smaller particles. The smaller particles may be introduced at the same time as the larger particles or as a slug of secondary particles.

A transparent tube of 0.6 cm in diameter and 50 cm length was used as a laboratory analogue to a fracture (see FIG. 6). Two differential pressure transducers were placed at either end of the tube.

Initially the tube was filled by the larger primary particles, 1 mm round particles, transported into the tube in a viscous slug (see FIG. 6). To enter the tube, particles had to pass through a 0.45 cm diameter front restriction. A viscous slug was necessary to avoid plugging of the front restriction; xanthan (700 cP@10, 1/s) was used for this purpose. The particles did not pass through the end restriction. The filling of primary particles was performed by gravity drainage. The plug length formed was about 24.5 cm at the end of the tube. A MRF of 700 was recorded using the primary particles only after flooding of the system with 500 ppm xanthan diluted in brine with a viscosity of 28 cP@10, 1/s.

The secondary particles, ≤0.2 mm diameter wood particles (7.2 wt %) were injected by a viscous slug consisting of 500 ppm xanthan. To obtain a homogeneous slug of secondary particles the injection was performed by co-injection of solvent (viscosifier) and wood chip paste and an inline mixer was used to combine the particles with the viscosifier (see FIG. 6, top image). Co-injection of the separate components of the slug is practical for adjusting the particle to viscosifier ratio during the experiments.

Figure 7:
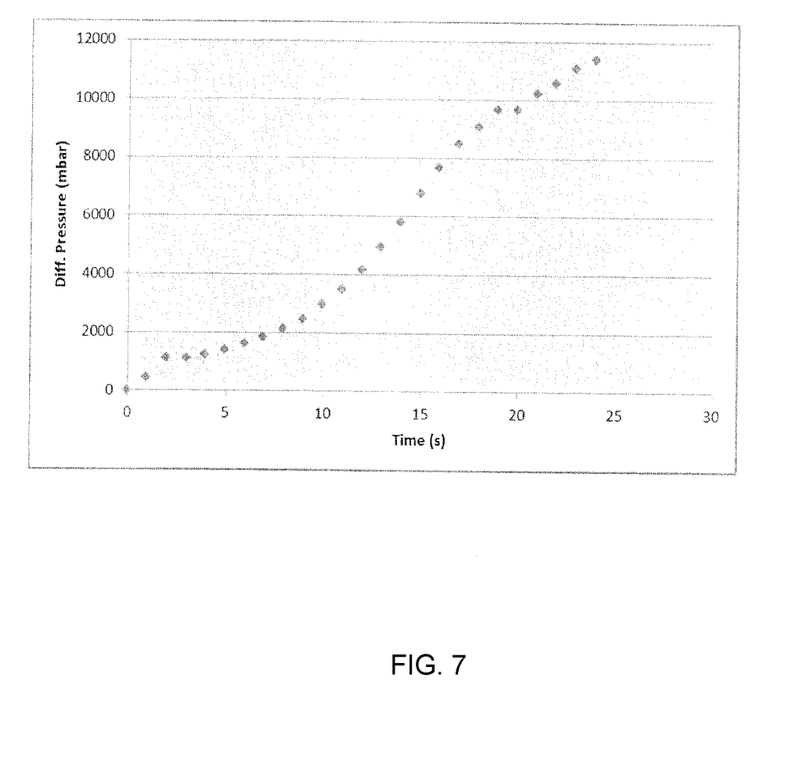
FIG. 7—is a graph showing pressure (mbar) over time (s) at a flow rate of 20 ml/min for a 2 component plug made up of 1 mm diameter particles and 0.2 mm diameter particles. The performed test indicated that the two component plug tested could withstand a pressure of 11400 mbar and above.

The introduction of secondary particles plugged in the first part (12.1 cm) of the plug measured by the DP1. The calculated MRF value, compared to the primary particle plug, was 728 for the first part of the plug (0-12.1 cm), demonstrating considerably decreased permeability compared to the primary plug alone FIG. 7 is a graph showing pressure (mbar) over time (s) at a flow rate of 20 ml/min for the 2 component plug made up of 1 mm particles and 0.2 mm particles. The performed test indicated that the two component plug can withstand a pressure of 11400 mbar and above.

The invention claimed is:

1. A method of establishing a plug in a hydrocarbon reservoir, the method comprising introducing into the reservoir a formulation comprising (A) solid particles, (B) microorganisms or cell-free enzymes, and (C) a viscosifier and then degrading said viscosifier, thereby reducing the viscosity of said formulation, and causing said solid particles to form a plug within said hydrocarbon reservoir; wherein the solid particles (i) are spherical, and (ii) have a core which is not deformable and an outer layer which is deformable; and wherein the viscosifier is a substrate for the microorganisms or cell-free enzymes.

2. The method as claimed in claim 1 wherein the microorganisms or cell-free enzymes are saccharolytic or lignocellulolytic.

3. The method as claimed in claim 2 wherein the microorganisms or cell-free enzymes are, or are from, *Clostridium thermocellum* or *Acidothermus cellulolyticus*.

4. The method of claim 1, wherein the viscosifier comprises, cellulose, hemicellulose or a derivative thereof or a polysaccharide gum.

5. The method as claimed in claim 4 wherein the viscosifier comprises a polyanionic cellulose or a microfibrillated cellulose.

6. The method as claimed in claim 5 wherein the viscosifier comprises carboxymethyl cellulose.

7. The method of claim 1, wherein the solid particles have the same density as the rest of the formulation.

8. The method of claim 1, wherein the solid particles are uniform in size.

9. The method of claim 1, wherein the formulation is made up of 25-70% by volume of the solid particles.

10. The method of claim 1, wherein the solid particles of the formulation comprise a first population of solid particles and a second population of solid particles, wherein said first population are at least five times larger than said second population.

11. The method of claim 1, wherein the solid particles of the formulation comprise a population of solid particles which are 0.05 to 5 mm in diameter.

12. The method of claim 1, wherein the solid particles of the formulation comprise a population of solid particles which are <0.2 mm but ≥1 µm in diameter.

13. The method of claim 1, wherein the formulation comprises a colloid comprising a continuous phase and a dispersed phase in which the solid particles are the dispersed phase.

14. The method of claim 1, wherein the formulation is an aqueous formulation.

15. The method of claim 1, wherein the formulation has a viscosity of 5-15 cPa.

16. The method of claim 1, wherein the microorganisms or cell-free enzymes degrade the viscosifier, thereby causing said solid particles to form the plug within the hydrocarbon reservoir.

17. The method of claim 1, said method further comprising introducing injection liquid into the reservoir in order to push the formulation to a target region within the reservoir.

18. A method of oil recovery from a hydrocarbon reservoir, which method comprises a method of establishing a plug as defined in claim 1, introducing injection liquid into said reservoir and recovering oil from said reservoir.

* * * * *